United States Patent
Addison et al.

(10) Patent No.: US 12,201,435 B2
(45) Date of Patent: Jan. 21, 2025

(54) VISION-BASED PATIENT STIMULUS MONITORING AND RESPONSE SYSTEM AND METHOD UTILIZING VISUAL IMAGES

(71) Applicant: Covidien LP, Mansfield, MA (US)

(72) Inventors: Paul S. Addison, Edinburgh (GB);
Dean Montgomery, Edinburgh (GB);
Philip C. Smit, Hamilton (GB)

(73) Assignee: COVIDIEN LP, Mansfield, MA (US)

( * ) Notice: Subject to any disclaimer, the term of this patent is extended or adjusted under 35 U.S.C. 154(b) by 670 days.

(21) Appl. No.: 17/376,701

(22) Filed: Jul. 15, 2021

(65) Prior Publication Data
US 2023/0012742 A1    Jan. 19, 2023

(51) Int. Cl.
| | | |
|---|---|---|
| *A61B 5/00* | (2006.01) | |
| *A61B 5/024* | (2006.01) | |
| *A61B 5/08* | (2006.01) | |
| *A61B 5/11* | (2006.01) | |
| *A61B 5/1171* | (2016.01) | |
| *A61B 5/1455* | (2006.01) | |

(52) U.S. Cl.
CPC ........ *A61B 5/4035* (2013.01); *A61B 5/02416* (2013.01); *A61B 5/0816* (2013.01); *A61B 5/1104* (2013.01); *A61B 5/1128* (2013.01); *A61B 5/1171* (2016.02); *A61B 5/14551* (2013.01); *A61B 2503/045* (2013.01)

(58) Field of Classification Search
CPC ...... G06V 10/00; G06V 40/00; A61B 5/0077; A61B 2576/00; A61B 5/0013
See application file for complete search history.

(56) References Cited

U.S. PATENT DOCUMENTS

| | | |
|---|---|---|
| 8,648,900 B2 | 2/2014 | Vu et al. |
| 10,757,366 B1 | 8/2020 | Kwatra et al. |
| 10,770,185 B2 | 9/2020 | Hayashi et al. |
| 2006/0049936 A1 | 3/2006 | Collins et al. |
| 2007/0040692 A1 | 2/2007 | Smith et al. |
| 2007/0157385 A1 | 7/2007 | Lemire et al. |
| 2010/0225501 A1 | 9/2010 | Grubis et al. |
| 2013/0109965 A1 | 5/2013 | Assman et al. |
| 2015/0199892 A1 | 7/2015 | Johnson et al. |
| 2017/0112504 A1 | 4/2017 | McEwen et al. |
| 2018/0348759 A1 | 12/2018 | Freeman et al. |
| 2019/0014982 A1 | 1/2019 | Bhuiyan |
| 2019/0231231 A1 | 8/2019 | Saria et al. |
| 2019/0320974 A1* | 10/2019 | Alzamzmi ............. A61B 5/746 |
| 2020/0046302 A1* | 2/2020 | Jacquel ................ A61B 5/0077 |

(Continued)

FOREIGN PATENT DOCUMENTS

| | | |
|---|---|---|
| KR | 20160124026 A | 10/2016 |
| WO | 2017139895 A1 | 8/2017 |

OTHER PUBLICATIONS

International Search Report and Written Opinion for PCT/US2022/036935 mailed Jan. 17, 2023, 13 pp.

*Primary Examiner* — Tse W Chen
*Assistant Examiner* — Michael A Catina
(74) *Attorney, Agent, or Firm* — Fletcher Yoder, P.C.

(57) ABSTRACT

Vision-based stimulus monitoring and response systems and methods are presented, wherein detection, via image(s) of a patient through an external stimulus, such as a caregiver, prompts analysis of the response of the patient, via secondary patient sensors or via analysis of patient image(s), to determine an autonomic nervous system (ANS) state.

20 Claims, 9 Drawing Sheets

(56) References Cited

U.S. PATENT DOCUMENTS

| | | |
|---|---|---|
| 2020/0121186 A1 | 4/2020 | Collins, Jr. et al. |
| 2020/0302825 A1 | 9/2020 | Sachs et al. |
| 2020/0329990 A1 | 10/2020 | Laszlo et al. |
| 2021/0065885 A1 | 3/2021 | Receveur et al. |
| 2021/0158965 A1 | 5/2021 | Receveur et al. |
| 2021/0272696 A1 | 9/2021 | Demazumder |
| 2021/0327245 A1* | 10/2021 | Addison ............... H04N 7/183 |
| 2021/0364589 A1 | 11/2021 | Bilgic et al. |
| 2022/0240790 A1 | 8/2022 | Smit et al. |

\* cited by examiner

VISION-BASED PATIENT STIMULUS MONITORING AND RESPONSE SYSTEM AND METHOD UTILIZING VISUAL IMAGES

FIELD

The present technology is generally related to a vision-based patient stimulus monitoring and response system utilizing visual images or image streams to detect stimulation of the patient by a caregiver with detection of a corresponding response from the patient.

BACKGROUND

For various patients, for example neonate patients, it can be difficult to ascertain whether that patient is in, or is about to enter, an impaired state indicative of disease, such as sepsis, among others.

Accordingly, there is a need in the art for improved techniques for determining whether a patient, be it a neonate or other, is in or is about to enter such impaired state.

SUMMARY

The techniques of this disclosure generally relate to vision-based patient stimulus monitoring and response systems and methods, wherein patient stimulation is detected via one or more images or image streams.

In one aspect, the present disclosure provides systems and methods that produces a localized measure of patient response to stimuli from which to accurately monitor that patient's autonomic nervous system ("ANS") state to determine whether the patient is in or is about to enter an impaired state (e.g., sepsis). Exemplary embodiments also find advantage in the art with regard to neonates, where such determinations may be more difficult otherwise. A lack of or a poor response may be indicative of the patient is in an impaired state whereas an energetic response may be indicative of a healthier state.

In exemplary embodiments systems and methods for determining an autonomic nervous system (ANS) state are provided, including: a camera configured to provide an image; a processor, including memory configured to store data; wherein the camera is configured to view an image of a patient, and wherein the camera and the processor are configured to provide image recognition to determine: identification of the patient; identification of external stimulation of the patient; and identification of cessation of stimulation of the patient; and further, wherein the processor is configured to use a parallel assessment of at least one physiological signal of the patient in time with the image recognized stimulation of the patient to assess a response to the stimulation of the patient in order to provide a measure of an autonomic nervous state (ANS) of the patient.

In further exemplary aspects, the disclosure provides a detector that is associated with a camera image or an image screen and detects stimulation of the patient by a caregiver. Once stimulation of the patient is detected, the patient response is measured, either via a physiological signal from a patient sensor or via the image.

In exemplary aspects related to measuring response via a patient sensor, such physiological sensor may be, for example, a heart rate signal from, e.g., a pulse oximeter probe, an electrocardiogram (ECG sensor), a blood pressure device, an accelerometer, a phonocardiogram, a device that records a cardiac waveform from which a heart rate or pulse rate can be derived, or any patient sensor providing a signal indicative of stimulation.

In exemplary aspects related to measuring response via the image (or image stream), patient response parameters may be collected and analyzed, as will be described in more detail below.

In additional exemplary aspects, the system and method described herein includes a processor that provides analysis, alarms and/or metrics.

Accordingly, such exemplary aspects provide systems and methods that determine a measure of response to stimulation of the patient that is directly related to observed stimulation.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

As we have noted above, the present disclosure describes vision-based patient stimulus monitoring and response systems and methods, wherein patient stimulation is detected via one or more images or image streams. Accordingly, such systems and methods determine a measure of response to stimulation of the patient that is directly related to observed stimulation.

In exemplary embodiments, a camera is configured to monitor a patient (e.g., a neonate), with an associated detector to identify whether a patient is being stimulated, e.g., by the hand of a caregiver. Identification of the stimulus, by the detector, triggers analysis of the response in order to provide a measure directly related to the observed stimulation.

For convenience, various examples such as those referred to with regard to FIGS. 1-9, refer to neonates and stimulation of neonates by a human caregiver, though it should be recognized that the present disclosure contemplates other patient types and other camera-detected sources of stimulation.

Figure 1:
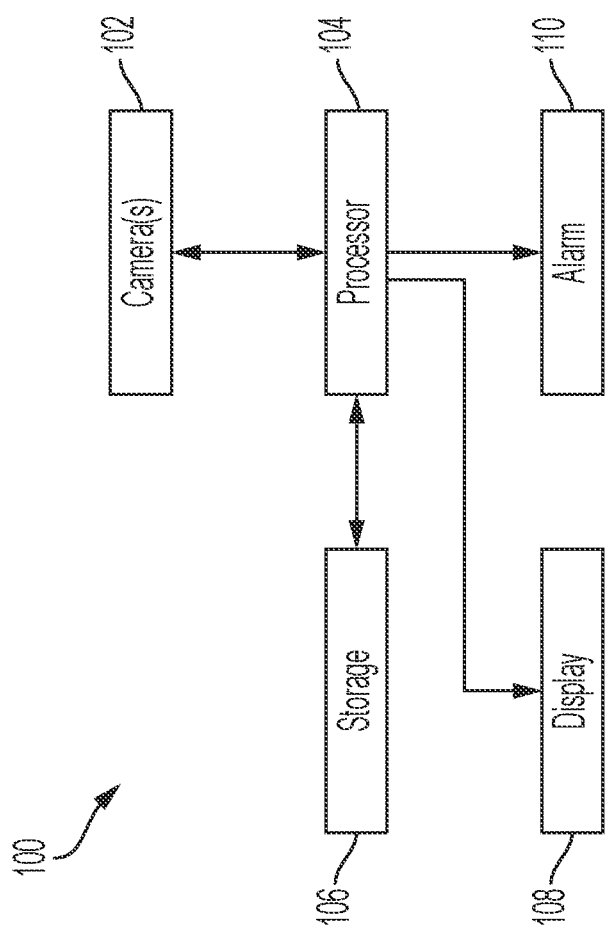
FIG. 1 is a diagram showing a schematic for an exemplary vision-based patient stimulus monitoring and response system and method in accordance with the present disclosure.

In one aspect, the present disclosure provides a system for vision-based patient stimulus monitoring using a camera and a processor to detect patient stimulus and to measure a response thereto relative to the patient's autonomic nervous system (ANS) to further determine whether the patient is in or is about to enter an impaired state indicative of disease. Referring to FIG. 1, the system 100 for patient monitoring includes at least one camera 102 that is configured to record an image or image stream of a neonate. Such camera(s) may detect RGB, IR, thermal and/or depth images and/or provide video streams. The data and information from the camera(s) is received and transmitted (via wired or wireless transmission) to a processor 104 (as part of a computing system, server, etc.), which is configured (alone or in conjunction with a complementary detector) to detect stimulation of the neonate by a caregiver in the image scene by analysis of the image(s) or image stream. The system may also include storage 106 for associated software, data storage, memory, etc., as well as a display for monitoring, administration, etc. Further, the processor may be configured to output one or more alarms, in accordance with aspects described below, e.g., should a neonate be in or be about to enter an impaired state.

In exemplary embodiments, the processor 104 is also configured to provide such calculations over time. The processor is optionally also configured to provide control functions for the camera(s). Data from the camera(s) and/or from processor calculations is optionally stored in memory/storage 106. Additionally, data from the camera(s) and/or from processor calculations is optionally transmitted for display on the display device 108. The processor is also optionally connected to alarm 110, which may activate during certain lapses with regard to defined limits.

Figure 2:
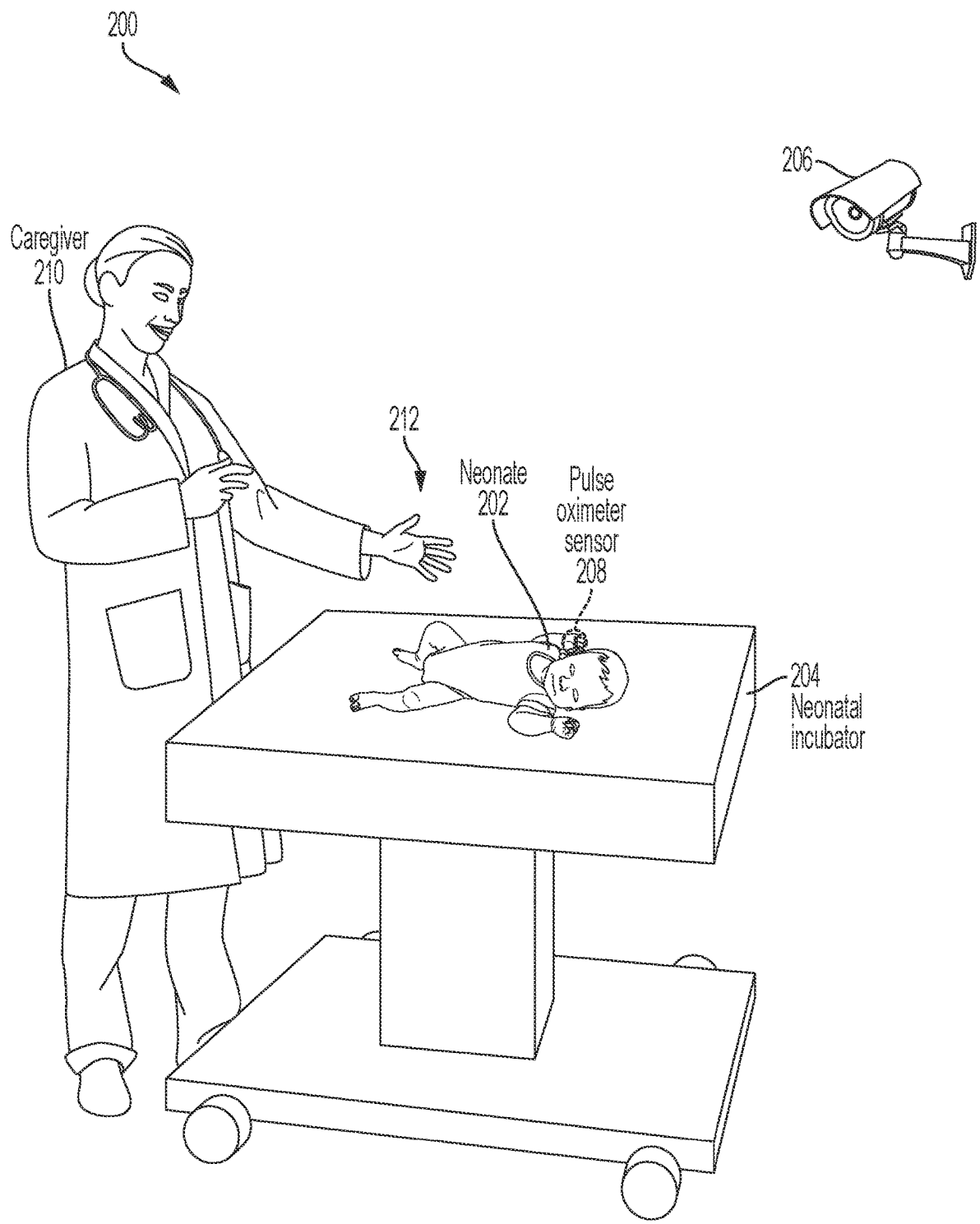
FIG. 2 is a conceptual diagram that illustrates an exemplary caregiver entering a neonate's incubator space, monitored by a camera.

In exemplary embodiments, the processor/detector 104 (FIG. 1) identifies within the image(s) or image stream body parts or aspects of a neonate, e.g., one or more of hands, a body, etc. provided within a bounded image of the patient, e.g., within the edges of the image, and in some embodiments, within defined portions of that image. FIG. 2 illustrates an exemplary illustration, generally at 200, of a neonate 202 in a neonatal incubator 204, monitored by a camera 206 and (optionally) a physiological sensor (pulse oximeter 208). A caregiver 210 is illustrated with arms 212 extended into the boundary of the neonatal incubator 204 monitored by camera 206.

In exemplary embodiments, such detection (e.g., of hands and/or feet of a neonate) is performed in accordance with deep learning routines, such as a YoLo deep learning algorithm, as described in commonly owned U.S. patent application Ser. No. 16/854,059, filed Apr. 21, 2020, the entire contents of which are expressly incorporated by reference herein.

Figure 3:
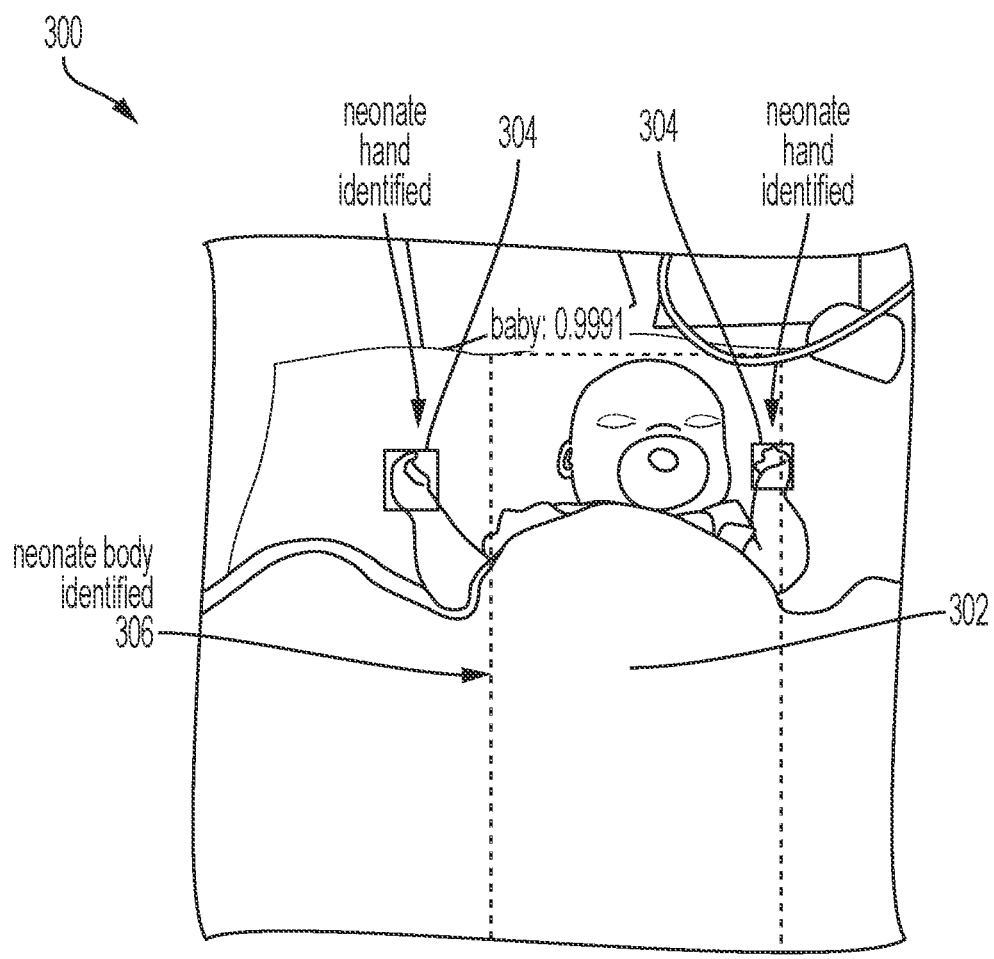
FIG. 3 is an elevation view of a neonate monitored by the camera of FIG. 2, with exemplary detection of neonate hands.

FIG. 3 illustrates at 300, identification of the hands 304 and/or body 306 of a neonate 302 by the image from camera 206 (FIG. 1), though the present disclosure also contemplates identification of other features of a neonate, including feet, facial features, etc.

Artificial intelligence models of varying types may be implemented to recognize objects within images or image streams, e.g. to place a box around recognized objects (multi-object classifiers), including YoLo, among others. For example, a classifier may be trained to detect hands using transfer learning. Additionally, a classifier may be trained (with a base or from scratch) to recognize other objects, e.g., a caregiver's hands.

Figure 4:
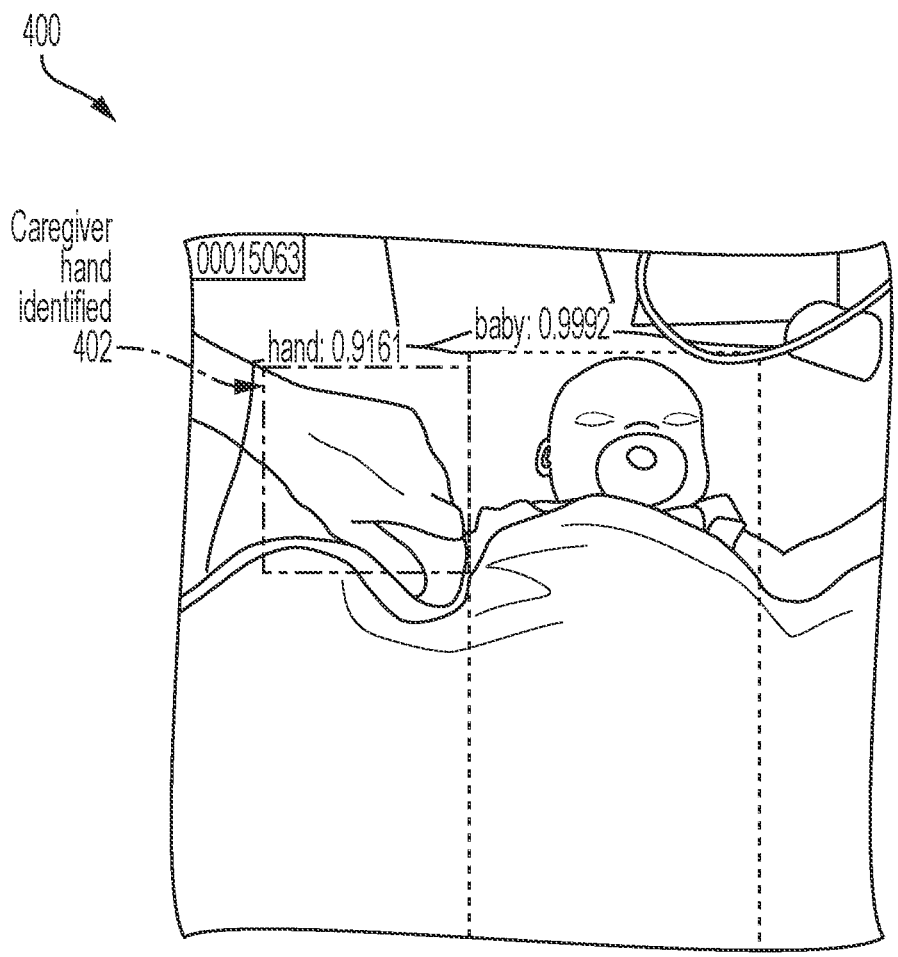
FIG. 4 is an elevation view of a neonate monitored by the camera of FIG. 2, with exemplary detection of a caretaker's hands.

With reference to FIG. 4, in further exemplary embodiments, detection of a caregiver is performed, generally at 400, for example of the caregiver's hand 402 (though other aspects of the caregiver may be detected) within the image of camera 206 (FIG. 1). In exemplary embodiments, the processor sets a stimulation flag (or other indicator) of such detection.

Figure 5:
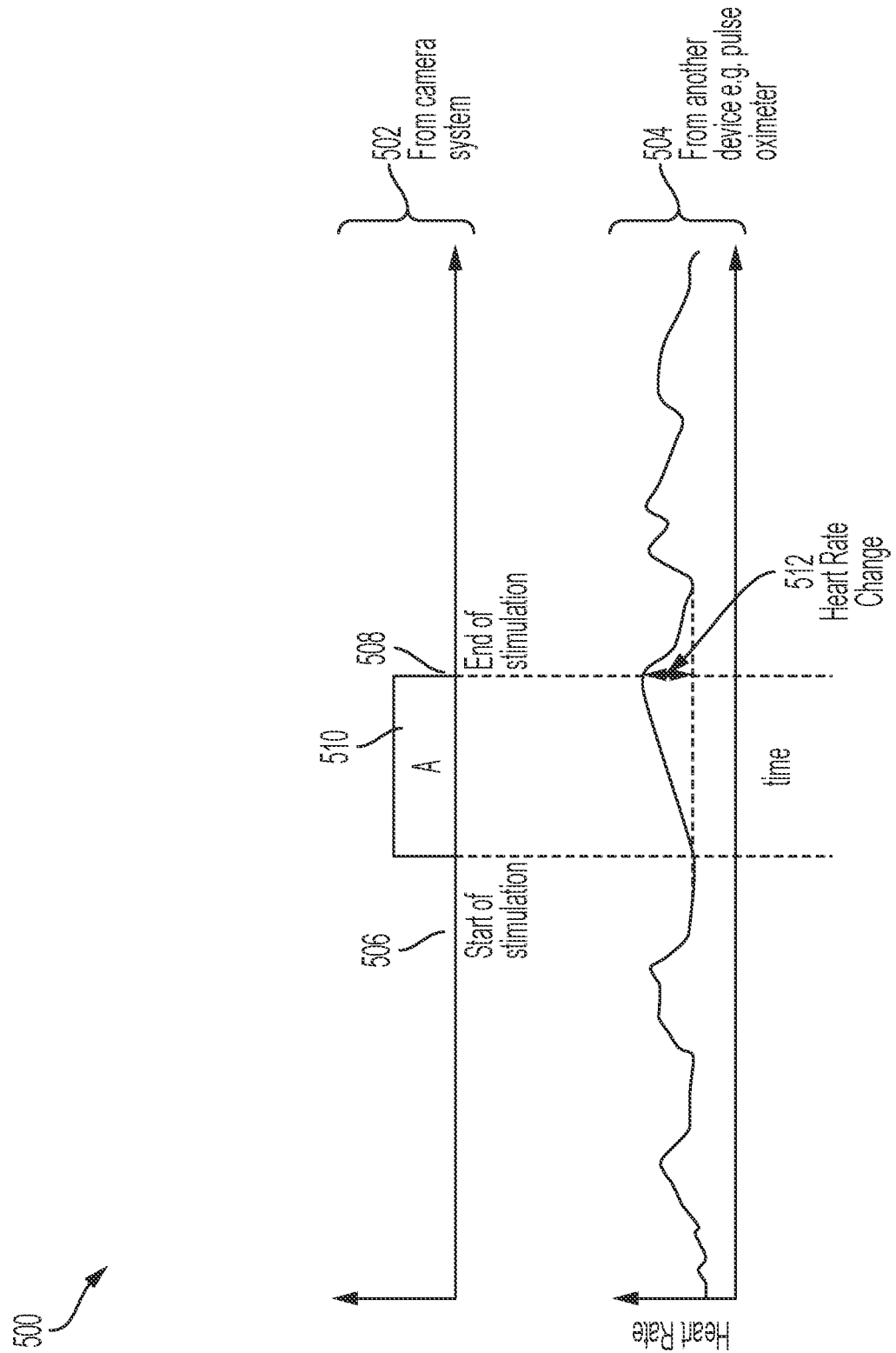
FIG. 5 is a diagram of parallel views of camera detection of stimulation of a neonate and detection of stimulation of that neonate.

FIG. 5 shows a time plot, generally at 500 of exemplary parallel monitoring of a patient via camera 206 (noting again that this could be via multiple cameras) and via a separate device, e.g., a pulse oximetry sensor. The exemplary cameral timeline is illustrated generally at 502 and the exemplary parallel pulse oximetry sensor timeline is shown generally at 504.

The camera system 502 illustrates a detected start of stimulation at 506, an end of stimulation 508, and a flag (A) set during stimulation at 510. Parallel to such detection, pulse oximeter 504 provides a signal indicative of heart rate (which is an exemplary physiological signal) over time, with a measured heart rate change 512 provided resultant from stimulation. We note that the measured heart rate change in this exemplary embodiment is measured as a difference from a start of stimulation 506 through the end of stimulation 508, though different portions, metrics or adjustments may be taken into account in the calculation of such difference/change 512.

As is noted above, in addition to detection of stimulation of a patient, parallel measurement of physiological signal(s) may be provided, including but not limited to heart rate, heart rate variability, respiration rate, blood pressure, oxygen saturation, an indication of perfusion, skin conductivity, etc.

It should be noted that the system and method may identify when a caregiver touches the neonate, taking into to account, for example, duration and location of physical contact (which may be usable to set an exemplary start of stimulation). For example, a short, one second touch may be, should the defined rules define it as such, not qualified as a start of stimulation, whereas a longer duration touch may qualify, dependent upon pre-set or defined rules. In such a way, a flag (or other indicator) would not be automatically set, e.g., according to that brief one touch, but would instead be set after a set or otherwise defined detected period of initial contact.

Figure 6:
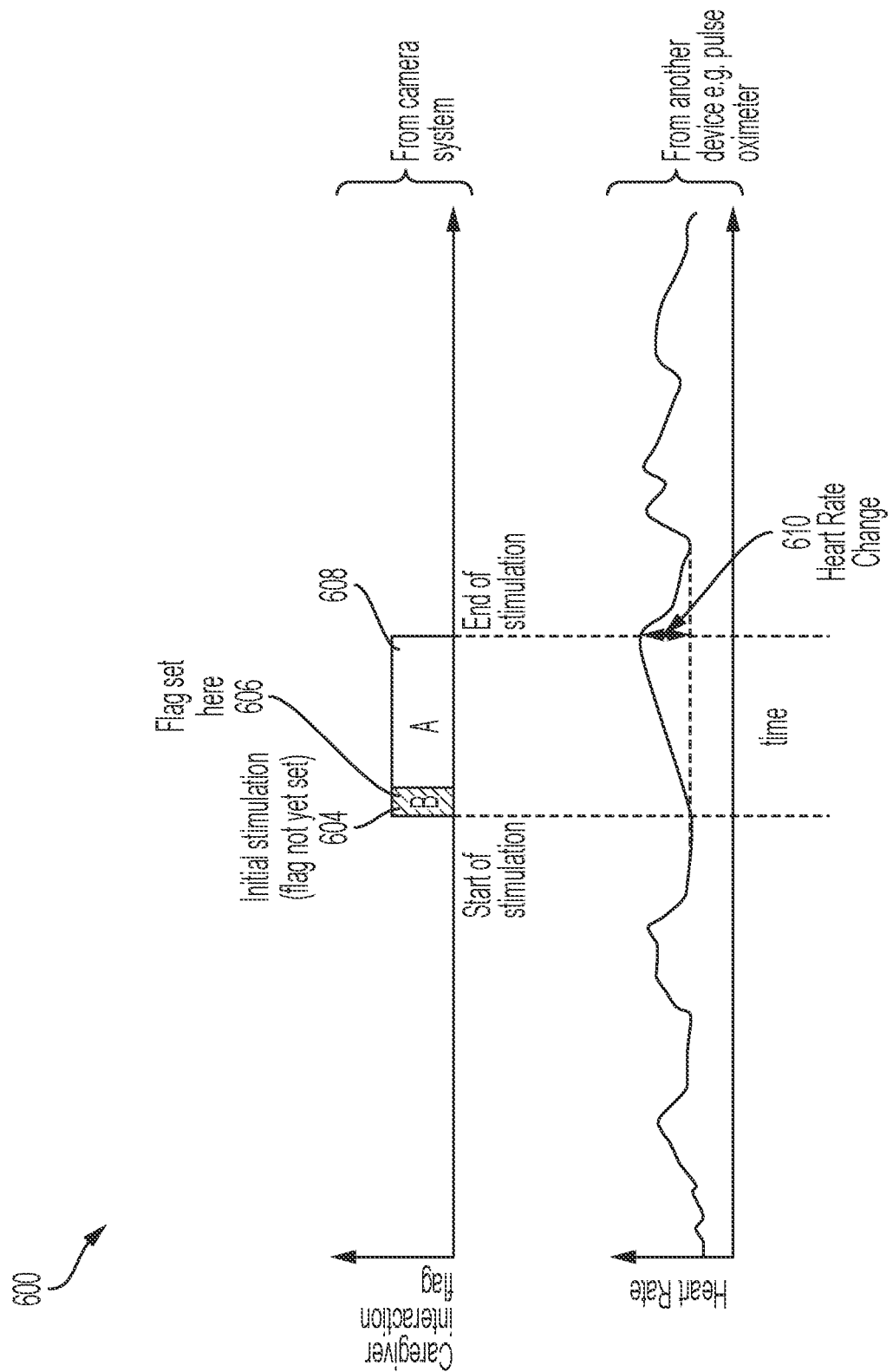
FIG. 6 is a diagram of parallel views of camera detection of stimulation of a neonate and detection of stimulation of that neonate.

FIG. 6 illustrates such an embodiment generally at 600, showing a caregiver interaction flag 602 instituted initially at 604, but not yet set (e.g., based upon factors discussed above, such as time/intensity of contact, as well as external factors, such as noise, that may or may not be filtered out). A flag (or other system prompt, action, calculation, etc.) is set upon satisfaction of criteria indicative of stimulation at 606. End of stimulation is similarly set at 608, though again, this could be a qualified end, based upon various factors, including removal of external stimuli (the caregiver's hands, for example), external noise, reduction of motion in the image or image stream, etc.

It should be noted that when looking at heart rate change, particularly with regard to setting the start of such change 610, such as in FIG. 6, change (in the illustrated FIG. 6) is measured according to the start of initial stimulation 604 (regardless of whether a flag is set). In other exemplary embodiments, measurement of such change starts with a primary point later in the timeline, e.g., up to and including when the flag is set at 606, which may adjust the value for the measured change 610.

It should also be noted that such a parallel measurement need not be discrete; and may be integrated into a running assessment of stimulation/response over time, either aggregated over all identified stimuli, or via subsets of identified stimuli of interest particular to ANS or other desired categories.

In exemplary embodiments, neonate (or other patient) stimulus can be accessed via the camera 206 and/or via additional cameras.

Figure 7:
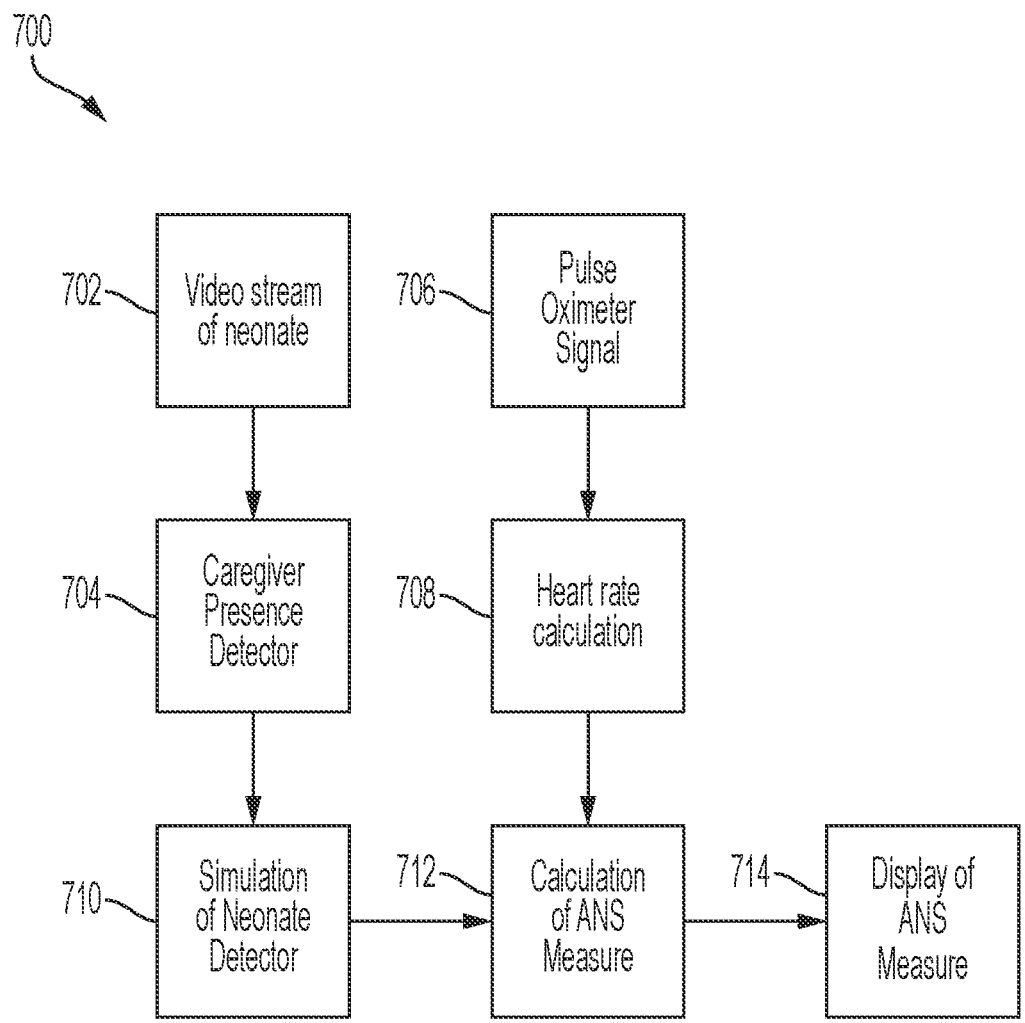
FIG. 7 is a flow diagram of parallel detection of patient stimulation and response for an ANS measure.

With reference to FIG. 7, in exemplary methods, heart rate variability ("HRV"), which may be measured during stimulus, can be determined via analysis of a video stream 702. We also refer to commonly owned U.S. Patent Application Ser. No. 63/145,503, Non-Contact Determination of Heart Rate using the Dot Projection Pattern Signal, filed Mar. 2, 2021, the entire contents of which are incorporated by reference herein, which techniques described therein apply herein. Caregiver detection is recognized at 704. In embodiments using parallel physiological sensors, an exemplary pulse oximeter is provided at 706. Heart rate calculation is provided at 708, via the pulse oximeter (noting that any response measure from any type of sensor may be utilized herein, relevant to ANS).

Referring still to FIG. 7, detection of neonate stimulation is indicated at 710, with a calculation of ANS measure at 712. Display of such measure is indicated at 714 (which may be by medical monitor, independent display using cast data, etc., including mobile or virtual displays), among others, provided integral to the system or to select parties or categories of parties, e.g., authorized personnel with regard to the data or data stream.

In such a way, the present disclosure provides a system and method for determining a measure of response to stimulation of a neonate (or other patient) directly related to the observed stimulation (with adjustable parameters). This permits localization of the measure in time and provides definable stimulation parameters. Additionally, noise, e.g., due to other factors such as loud noise, a neonate simply waking up independently of a caregiver, apneic episodes, the neonate changing positions in bed, etc., can be excluded.

It should be noted that an ANS heart rate measure may be one or more of, without exclusion: variability of heart rate; the change in heart rate due to stimulus; the time to return to baseline heart rate after stimulus, the rate of return to baseline heart rate after stimulus (delta HR/time), the rate of increase from a baseline heart rate at the start of stimulation, etc.

In further exemplary embodiments, the length of intervention may be used to normalize the return to baseline. For example, a long intervention may cause more of a significant change in heart rate, with normalization of the ANS measure being performed accordingly.

It should also be noted that HRV measurements during stimulus may also be compared to patient (again, e.g., neonatal) HRV in the non-stimulated state for context or qualification. Further, in exemplary embodiments, the period of time of activity after the end of stimulus may also provide context or measure of neonatal ANS.

We refer again to commonly owned U.S. Patent Application Ser. No. 63/145,403, filed Mar. 2, 2021, which describes techniques for: Non-Contact Determination of Heart Rate using Dot Projection Pattern Signals, the contents of which are specifically incorporated herein by reference. As such, in exemplary embodiments, a parallel measure of response may be correlated with the applied determined stimulus.

Figure 8:
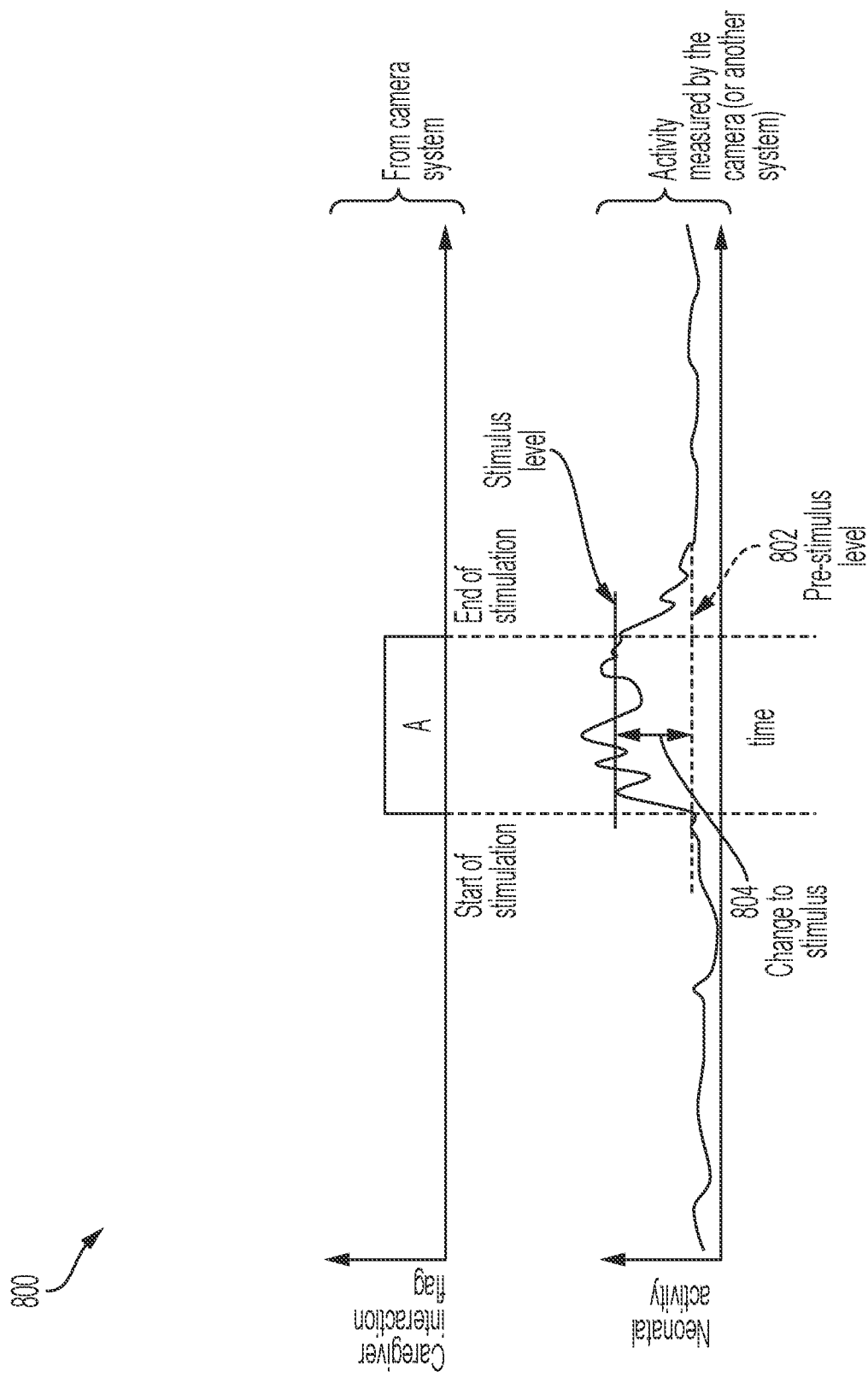
FIG. 8 is diagram of parallel views of camera detection of stimulation of a neonate and detection of stimulation of that neonate.

Additionally, in exemplary embodiments, a direct measure of activity from a neonate can be measured from the video stream, for example by following fiducial points on the neonate, or by measuring gross changes in pixel values within a region, for example. The degree of activity may be used as an ANS measure, e.g., as depicted in FIG. 8. For example, a pre-stimulus baseline may be measured (note pre-stimulus level 802) relative to a measured change in stimulus 804.

Figure 9:
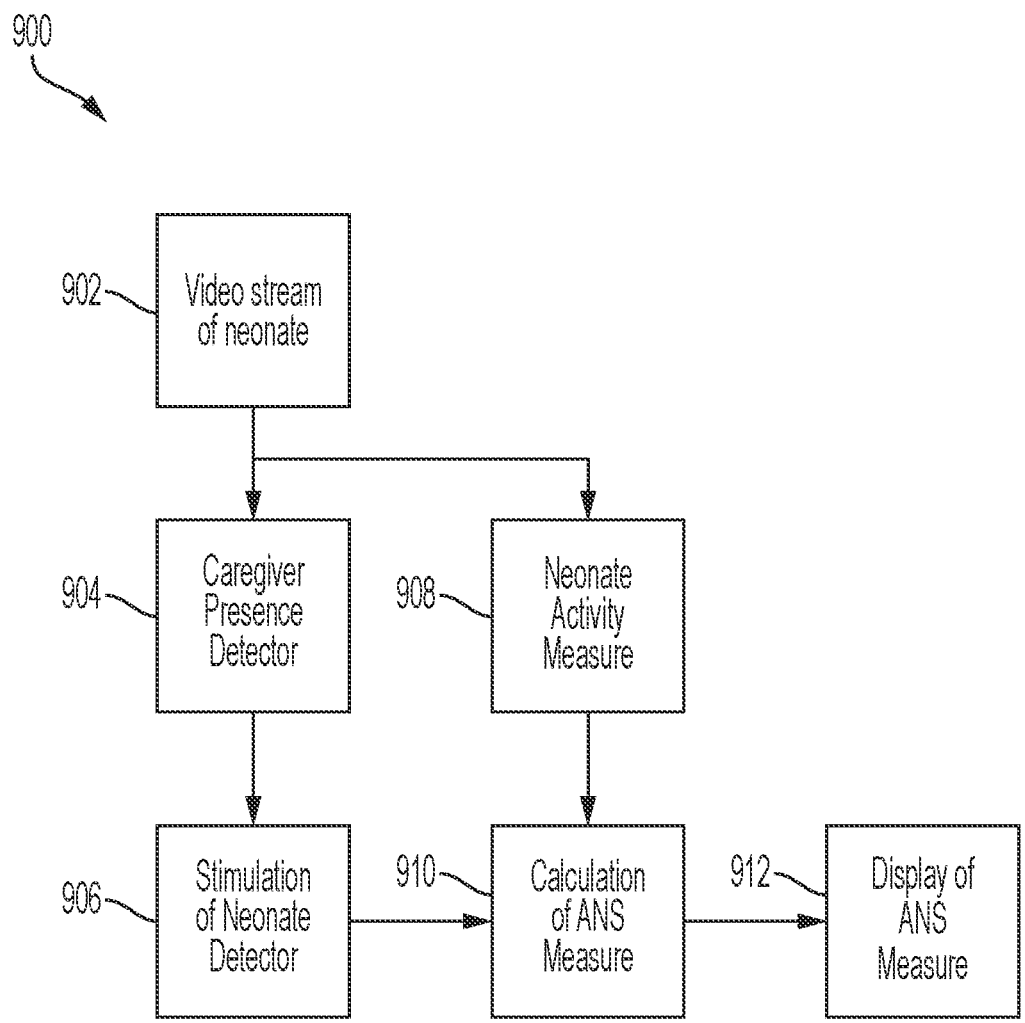
FIG. 9 is a flow diagram of parallel detection of patient stimulation and response for an ANS measure, with a pre-stimulus measure.

FIG. 9 illustrates a flow chart, generally at 900, of generation of a video stream of a neonate 902, detection of caregiver presence 904, and detection of stimulation of the neonate 906. Calculation of an ANS measure for the neonate 910, in exemplary embodiments, takes into account a baseline measurement of neonate activity 908. Optional display of ANS measure is illustrated at 912.

It should be noted that while the present disclosure relates to heart rate or heart rate variability (or indeed, response indicated by the video image or image stream), any other measurable physiological measure applicable to stimulus response is contemplated herein. For example, respiration rate (RR) of a neonate (or other patient) can serve as a measure of response as disclosed herein. For various possible responses, baselines may be created, updated, etc., to provide accurate measures in line with the above. With regard to RR, for example, a pre-stimulus baseline may be measured. When the stimulus occurs, the RR may increase. A measure of this change may be made. The RR may be measured from the pulse oximetry waveform, from the video stream, or from any other device configured to measure RR.

Accordingly, and advantageously, such systems and methods provide mechanisms to determine whether a patient is in or is about to enter an impaired state indicative of disease.

The present disclosure relates to use of any camera system, or combination of camera systems, where a distance or depth can be measured, including infrared (IR) and Red/Green/Blue (RGB), etc. Additionally, the camera(s) may generate distance or depth data independently, or with the assistance of one or more processors in communication therewith.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system for determining an autonomic nervous system (ANS) state, comprising:
    a camera to generate image data of a patient;
    a display;
    a memory that stores machine executable instructions; and
    a processor coupled to the memory, the display, and the camera, wherein the processor executes the machine executable instructions to:
        receive the image data indicative of the patient from the camera;
        receive a physiological signal of the patient from a sensor coupled to the patient;
        identify the patient in the image data based on at least one patient feature in the image data;
        identify a first time corresponding to a start of physical contact between a caregiver and the patient based on the image data;
        determine that a duration of the physical contact extends from the first time to a second time based on the image data;
        in response to determining that the duration of the physical contact exceeds a threshold, set an interaction flag to indicate that the physical contact qualifies as an external stimulation to the patient;
        in response to setting the interaction flag, continue to monitor the physical contact to identify a third time corresponding to cessation of the physical contact based on the image data and determine a measure of an autonomic nervous state (ANS) of the patient based on a response of the patient to the physical contact between the first time and the third time, wherein the response comprises patient activity of the patient based on the image data and a change in a physiological parameter of the patient based on the physiological signal of the patient; and
        instruct the display to output the measure of the ANS of the patient.

2. The system of claim 1, wherein the image data includes a bounded image of the patient; and wherein the processor is configured to identify the at least one patient feature based on the bounded image.

3. The system of claim 2, wherein the processor executes the machine executable instructions to identify the physical contact between the caregiver and the patient within the bounded image.

4. The system of claim 1, wherein the processor executes the machine executable instructions to log the duration of the physical contact from the first time to the second time.

5. The system of claim 1, wherein the at least one patient feature comprises a hand, a body, a face, or a foot of the patient.

6. The system of claim 1, wherein the processor executes the machine executable instructions to identify a hand of the caregiver within the image data.

7. The system of claim 1, wherein the processor executes the machine executable instructions to:
    identify the physical contact within the image data, wherein the physical contact comprises a hand of the caregiver interacting with the patient; and
    measure the patient activity of the patient based on the image data.

8. The system of claim 1, wherein the physiological parameter comprises a heart rate variability (HRV), respiration rate (RR), or both.

9. A method for determining an autonomic nervous system (ANS) state, comprising:
    receive, via a system comprising a processor and a memory, image data indicative of a patient from a camera;
    receive, via the system, a physiological signal of the patient from a sensor coupled to the patient;
    identify, via the system, the patient in the image data based on at least one patient feature in the image data;
    identify, via the system, a first time corresponding to initiation of physical contact between a caregiver and the patient within the image data;
    determine, via the system, that a duration of the physical contact extends from the first time to a second time based on the image data;
    set, via the system and in response to determining that the duration of the physical contact exceeds a threshold, an interaction flag to indicate that the physical contact qualifies as an external stimulation to the patient;
    identify, via the system and after setting the interaction flag, a third time corresponding to cessation of the physical contact of the patient within the image data;
    determine, via the system and after setting the interaction flag, an autonomic nervous state (ANS) of the patient based on a response of the patient to the physical contact between the first time and the third time, wherein the response comprises patient activity of the patient based on the image data and a change in a physiological parameter of the patient based on the physiological signal; and
    output, via the system and a display, an indication of the ANS of the patient.

10. The method of claim 9, comprising:
    identify, via the system, the at least one patient feature of the patient in the image data; and
    overlay, via the system, at least one box over the at least one patient feature of the patient in the image data.

11. The method of claim 10, comprising:
    identify, via the system, a hand of the caregiver within the at least one box to identify the physical contact between the caregiver and the patient within the image data within the at least one box.

12. The method of claim 9, comprising:
store, via the system, the first time corresponding to a start time of the external stimulation of the patient; and
store, via the system, the third time corresponding to an end time of the external stimulation of the patient.

13. The method of claim 9, wherein the at least one patient feature comprises a hand, a body, a face, or a foot of the patient.

14. The method of claim 9, comprising:
identify, via the system, a hand of the caregiver within the image data to identify the physical contact between the caregiver and the patient within the image data.

15. The method of claim 14, comprising:
determine, via the system and during the physical contact, the response of the patient to the physical contact.

16. The method of claim 9, wherein the physiological parameter comprises a heart rate variability (HRV), a respiration rate (RR), or both.

17. The method of claim 9, comprising:
determine, via the system, a first amount of patient activity of the patient within the image data prior to the first time;
determine, via the system, a second amount of patient activity of the patient within the image data between the first time and the third time; and
determine, via the system, the response of the patient based on the first amount of patient activity and the second amount of patient activity.

18. The system of claim 1, wherein the processor executes the machine executable instructions to:
in response to determining that the duration of the physical contact does not exceed the threshold, do not set the interaction flag and continue to analyze the image data to identify a subsequent start of additional physical contact between the caregiver and the patient.

19. The system of claim 1, wherein the processor executes the machine executable instructions to identify the third time based on identifying removal of a hand of the caregiver from the image data.

20. The method of claim 9, comprising:
identify, via the system and after setting the interaction flag, the third time based on identifying removal of a hand of the caregiver from the image data.

\* \* \* \* \*